(12) United States Patent
Kim et al.

(10) Patent No.: US 7,692,794 B2
(45) Date of Patent: Apr. 6, 2010

(54) OPTICAL DETECTION APPARATUS, OPTICAL DETECTION METHOD, AND MICROFLUIDIC SYSTEM INCLUDING THE OPTICAL DETECTION APPARATUS

(75) Inventors: Su-hyeon Kim, Seoul (KR); Jeong-gun Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 40 days.

(21) Appl. No.: 11/972,266

(22) Filed: Jan. 10, 2008

(65) Prior Publication Data

US 2009/0021741 A1    Jan. 22, 2009

(30) Foreign Application Priority Data

Jul. 20, 2007    (KR) ...................... 10-2007-0073116

(51) Int. Cl.
*G01N 21/25* (2006.01)
(52) U.S. Cl. ..................................... 356/418
(58) Field of Classification Search ................. 356/440, 356/418, 435, 39; 435/14, 286.4, 288.7, 435/7.21, 287.2; 250/564; 436/45
See application file for complete search history.

(56) References Cited

U.S. PATENT DOCUMENTS

| | | | |
|---|---|---|---|
| 3,697,185 A * | 10/1972 | Kassel et al. ................. 356/410 |
| 4,477,190 A * | 10/1984 | Liston et al. ................. 356/418 |
| 4,488,810 A * | 12/1984 | Hatanaka et al. ............ 356/244 |
| 6,429,936 B1 * | 8/2002 | Scaduto ....................... 356/417 |
| 7,274,455 B2 * | 9/2007 | Ok et al. ...................... 356/417 |
| 2006/0050277 A1 * | 3/2006 | Ok et al. ...................... 356/417 |
| 2006/0202133 A1 * | 9/2006 | Ok et al. .................. 250/458.1 |
| 2007/0077605 A1 * | 4/2007 | Hurt et al. .................. 435/7.21 |
| 2008/0273205 A1 * | 11/2008 | Lee et al. ..................... 356/440 |

* cited by examiner

*Primary Examiner*—Tarifur R. Chowdhury
*Assistant Examiner*—Isiaka O Akanbi
(74) *Attorney, Agent, or Firm*—Sughrue Mion, PLLC

(57) ABSTRACT

Provided are an optical detection apparatus, a microfluidic system including the same, and an optical detection method. The optical detection apparatus including: at least one light emission unit which emits light of a predetermined wavelength band; at least one light receiving unit which is disposed such that the light receiving unit receives the light emitted from the light emission unit and generates an electrical signal according to the intensity of the light received, wherein the number of light receiving units is the same as the number of light emission units; a rotation operating unit which rotates a disk-type microfluidic apparatus comprising at least one detection chamber in which a sample is to be loaded such that the detection chamber is disposed in a light pathway between the light emission unit and the light receiving unit; and a processor which measures a property of the sample contained in the detection chamber using the electrical signal generated by the light receiving unit.

26 Claims, 5 Drawing Sheets

OPTICAL DETECTION APPARATUS, OPTICAL DETECTION METHOD, AND MICROFLUIDIC SYSTEM INCLUDING THE OPTICAL DETECTION APPARATUS

CROSS-REFERENCE TO RELATED PATENT APPLICATIONS

This application claims the benefit of Korean Patent Application No. 10-2007-0073116, filed on Jul. 20, 2007, in the Korean Intellectual Property Office, the disclosure of which is incorporated herein in its entirety by reference.

BACKGROUND OF THE INVENTION

1. Field of the Invention

The present invention relates to an optical detection apparatus for detecting the concentration of a specific component in a biochemical sample using an optical method, an optical detection method, and a microfluidic system including the optical detection apparatus.

2. Description of the Related Art

In the field of microfluidics, conventionally, a microfluidic apparatus which is used in processes using a small amount of a fluid includes a chamber which stores a small amount of a fluid, a channel through which the fluid flows, and a valve which controls the flow of the fluid. A bio-chip is an apparatus in which an assay including a biochemical reaction can be performed on a small chip. Specifically, an apparatus in which many processes are performed to treat and manipulate a fluid on a single chip is referred to as a lab-on-a-chip.

In microfluidic apparatuses, a fluid flows due to an operating pressure. The operating pressure can be a capillary pressure or a pressure generated by a separate pump. Recently, disk-type microfluidic apparatuses in which a fluid flows by a centrifugal force generated when a microfluidic apparatus having a disk-like shape including a chamber and a channel rotates has been developed. Such disk-type microfluidic apparatuses are referred to as Lab CD or Lab-on-a-CD.

Results of biochemical assay, immunoassay, or gene assay which is performed in a disk-type microfluidic apparatus can be detected using an optical detection apparatus. A conventional optical detection apparatus utilizes a filter wheel to select a desired wave, utilizes a spectrograph and an array-shaped photo detector, such as CCD, or utilizes a plurality of mirrors and bandpass filters to separate light emitted from a light source into wavelength bands. However, such optical detection apparatuses require expensive optical components and thus the price thereof is high. In addition, a long time is required to detect results of various processes which are performed using the disk-type microfluidic apparatus.

SUMMARY OF THE INVENTION

The present invention provides an optical detection apparatus which can detect results of various reactions which are performed in a microfluidic apparatus in a short time and are inexpensive, an optical detection method, and a microfluidic system including the optical detection apparatus.

According to an aspect of the present invention, there is provided an optical detection apparatus including: at least one light emission unit which emits light of a predetermined wavelength band; at least one light receiving unit which is disposed such that the light receiving unit receives the light emitted from the light emission unit and generates an electrical signal according to the intensity of the light received, wherein the number of the light receiving unit is the same as the number of the light emission unit; a rotation operating unit which rotates a disk-type microfluidic apparatus including at least one detection chamber in which a sample is to be loaded and at least one blank chamber in which a reference fluid is to be loaded, the rotation being performed such that the detection chamber and the blank chamber are disposed in a light pathway between the light emission unit and the light receiving unit; and a processor which measures a property of the sample contained in the detection chamber using the electrical signal generated in the light receiving unit.

The optical detection apparatus includes a plurality of light emission unit-light receiving unit pairs corresponding to the light emission unit so that light is simultaneously emitted to at least some of the detection chambers of the disk-type microfluidic apparatus and an electrical signal corresponding to the light emitted is obtained, wherein the light emission units emit light of different wavelength bands from each other.

The plurality of light emission unit-light receiving unit pairs are disposed at equidistant intervals on a circular arc having the same center as a rotation center of the disk-type microfluidic apparatus.

When the disk-type microfluidic apparatus rotates one complete rotation, each of the detection chambers of the disk-type microfluidic apparatus is sequentially exposed to lights emitted from all of the light emission units.

The light emission unit includes a light emitting diode (LED).

The light receiving unit includes a photo diode.

The light emission unit further includes a lens which focuses light into an active area of a photo diode.

The light receiving unit further includes a filtering portion which reduces a width of a wavelength band of light emitted from the light emission unit.

The filtering portion includes a long wave pass filter which allows passage of light of a wavelength band which includes a target wavelength and a wavelength longer than the target wavelength, and a short wave pass filter which allows passage of light of a wavelength band which includes a target wavelength and a wavelength shorter than the target wavelength.

The processor measures intensity of the light passed through the detection chamber.

The absorbance can be calculated by measuring intensity of the light passed through the detection chamber and reference chamber, such as water filled blank chamber. Absorbance can be defined as $A_\lambda = \log(I/I_0)$, where I is the intensity of light at a specified wavelength $\lambda$ that has passed through a detection chamber and $I_0$ is the intensity of light at a specified wavelength $\lambda$ that has passed through a blank chamber.

The property of the sample determined by the apparatus is a concentration of a specific component measured on the basis of absorbance of the sample proportional to the concentration of the specific component.

According to another aspect of the present invention, there is provided optical detection method including: positioning a detection chamber of a disk-type microfluidic apparatus containing a sample in a light pathway between a light emission unit and a light receiving unit; emitting light of a predetermined wavelength band to the detection chamber, using the light emission unit; receiving the light which has passed through the detection chamber and converting the light into an electrical signal, using the light receiving unit; and measuring a property of the sample contained in the detection chamber using an electrical signal.

The disk-type microfluidic apparatus includes a plurality of detection chambers, a plural pair of the light emission unit and the light receiving unit, wherein the light emission units emit lights of different wavelength bands from each other and the light receiving units receives the lights emitted, the positioning is performed such that at least some of the detection chambers of the disk-type microfluidic apparatus are positioned in light pathways between the plural pair of the light emission unit and the light receiving unit, the emitting is performed such that the light emission units simultaneously emit light of different wavelength bands from each other to at least some of the detection chambers, the receiving of light is performed such that the light receiving units convert the light which has passed through at least some of the detection chambers into an electrical signal, and the measuring is performed such that a property of a sample contained in the at least some of the detection chambers is measured using the electrical signal.

The detection chambers are disposed at equidistant intervals on a circular arc having the same center as a rotation center of the disk-type microfluidic apparatus, and during the disk-type microfluidic apparatus rotates one complete rotation, each of the detection chambers of the disk-type microfluidic apparatus is sequentially exposed to lights of all the light emission units.

In the measuring, intensity of the light passed through the detection chamber is measured.

After the measuring, absorbance of the detection chamber is calculated and a concentration of a specific components contained in the sample is determined on the basis of the absorbance According to the present invention, the manufacturing costs can be reduced because there is no need to use expensive optical components, such as a filter wheel. In addition, when various kinds of reactions are performed using a sample, the results can be obtained immediately. Accordingly, examinations for diagnosis and treatment of a patent can be performed in a reduced time, and especially, lives of urgent patients can be protected and their medical states can be improved.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
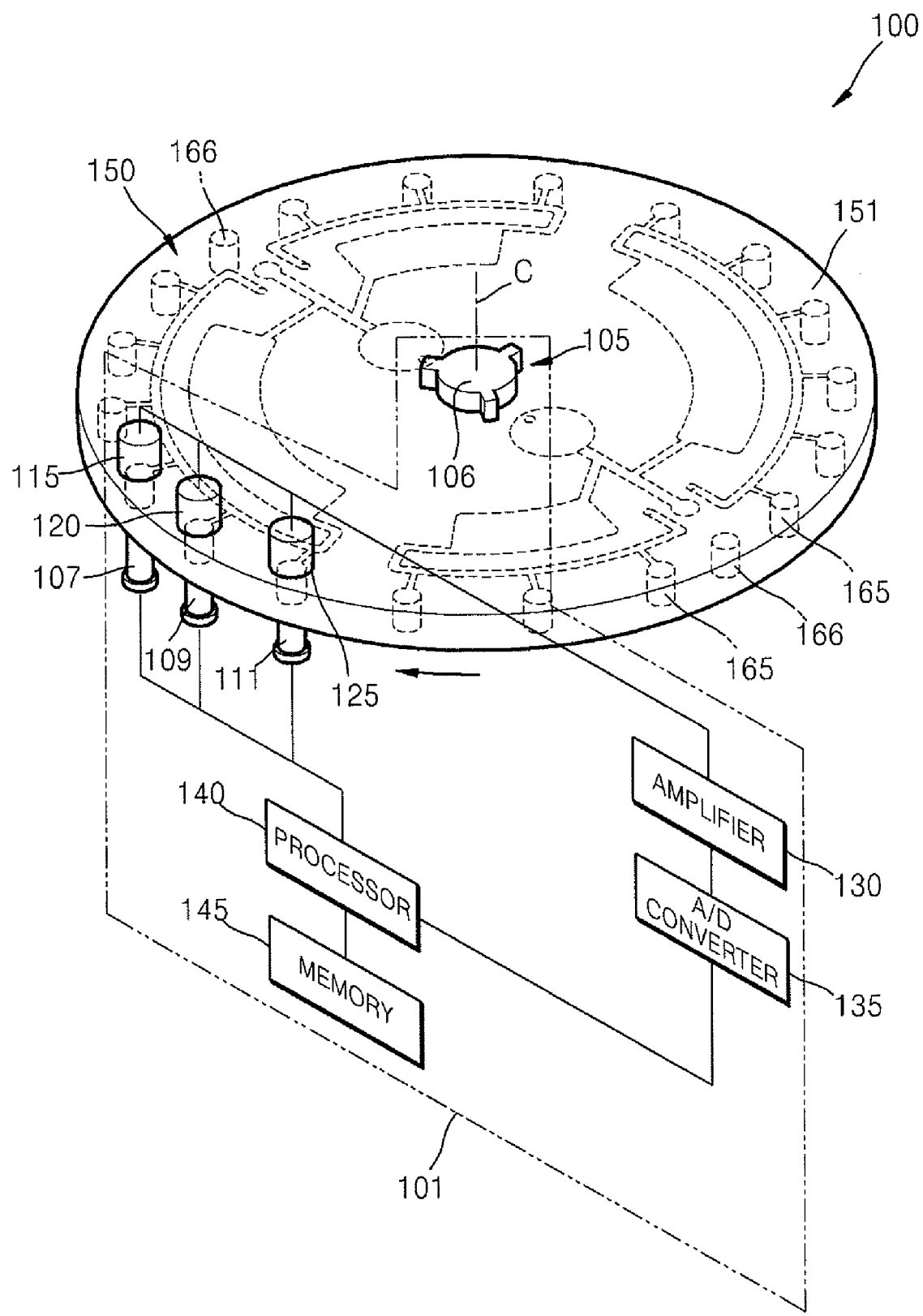
FIG. 1 is a perspective view of a microfluidic system according to an embodiment of the present invention.
Figure 2:
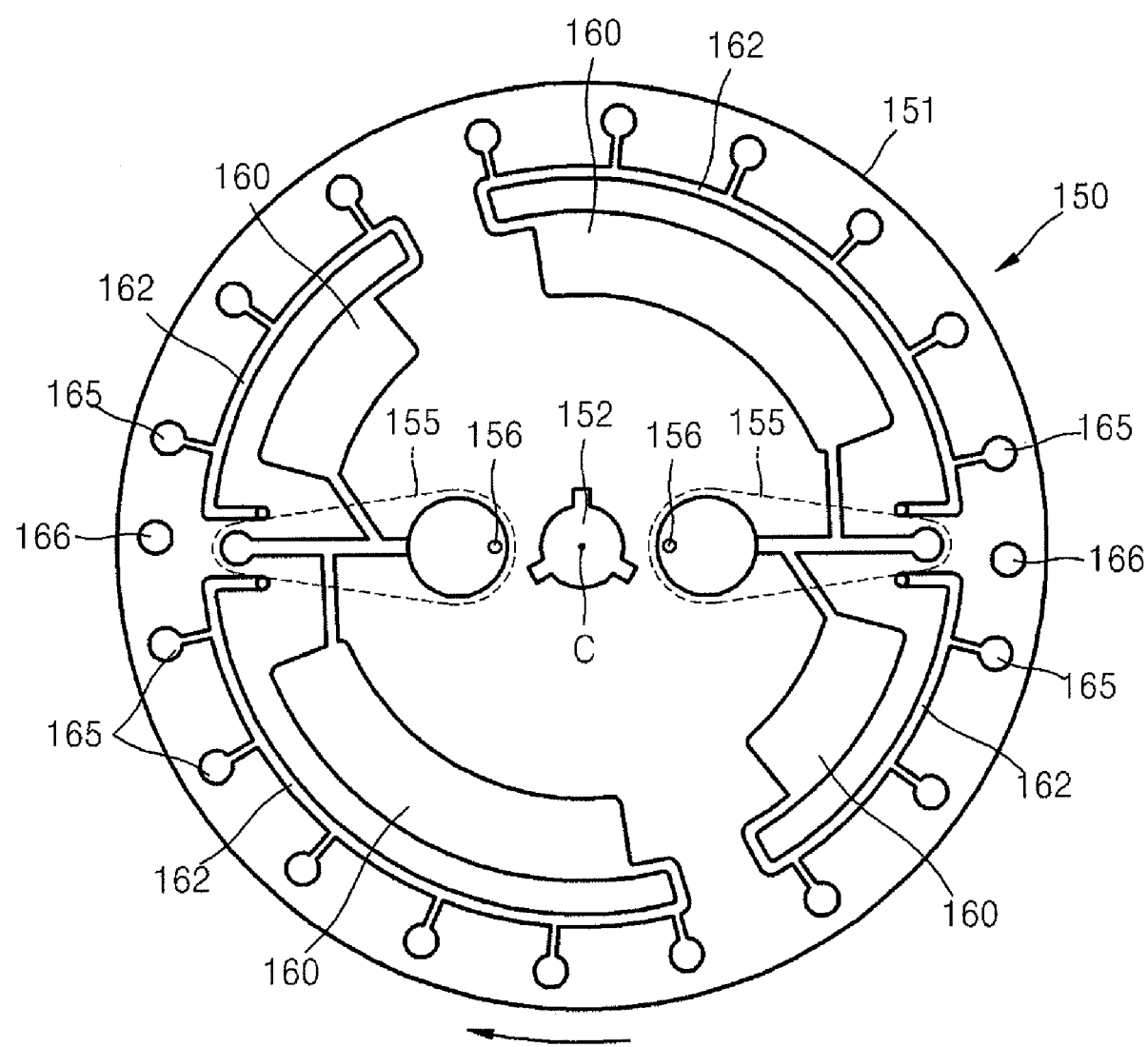
FIG. 2 is a plan view of a disk-type microfluidic apparatus of the microfluidic system of FIG. 1.

FIG. 1 is a perspective view of a microfluidic system 100 according to an embodiment of the present invention, and FIG. 2 is a plan view of a disk-type microfluidic apparatus 150 of the microfluidic system of FIG. 1.

Referring to FIG. 1, the microfluidic system 100 includes the disk-type microfluidic apparatus 150, and an optical detection apparatus 101 which optically measures properties of a sample contained in a detection chamber 165 of the disk-type microfluidic apparatus 150. The disk-type microfluidic apparatus 150 includes structures for the centrifugal separation, distribution, and biochemical reactions of a sample on a disk-like platform 151.

The disk-type platform 151 can be made of a plastic material that is easily handled to obtain a desired shape, optically transparent, and biologically inactive. Examples of such a plastic material include polymethyl methacrylate (PMMA), polydimethylsiloxane (PDMS), and polycarbonate (PC). However, a material for forming the disk-type platform 151 is not limited. For example, the disk-type platform 151 can be formed using any material that is biochemically stable, optically transparent, and mechanically processable. The disk-type platform 151 may consists of a plurality of planes. Intaglio structures corresponding to chambers and/or channels are formed in facing surfaces of respective planes, and then the planes are bound together, thereby forming spaces and/or passages, which respectively corresponds to chambers and/or channels, inside the disk-type platform 151. Planes can be adhered to each other using, for example, an adhesive or a double-sided adhesive tape, ultrasonic fusion, or laser welding.

The disk-type microfluidic apparatus 150 illustrated in FIG. 2 is an example of a simple microfluidic apparatus in which various biochemical assays are simultaneously performed in a single disk-type platform. A biochemical assay is performed to detect a specific target material through a biochemical reaction between a reagent and a biosample, such as blood, serum separated from blood, urine, or sputum. Referring to FIG. 2, the disk-type microfluidic apparatus 150 includes a spindle mount groove 152 in its middle portion, a pair of centrifugal separation unit 155, two pairs of sample dilution chambers 160, distribution channels 162, a plurality of detection chambers 165, and blank chambers 166.

The centrifugal separation unit 155 can extract serum from blood. Each centrifugal separation unit 155 includes an injection hole 156 through which a blood is injected to the centrifugal separation unit 155. The sample dilution chambers 160 store diluting solution and the centrifugally separated serum is mixed with the diluting solution in the chamber. The diluted serum contained in the sample chambers 160 moves to the detection chambers 165 disposed in a peripheral area of the disk-type microfluidic apparatus 150 through the distribution channel 162. The centrifugal separation, the movement of the serum from the centrifugal separation unit 155 to the sample dilution chambers 160, and the movement of the serum from the sample dilution chambers 160 to the detection chambers 165 occur due to a centrifugal force generated when the disk-type microfluidic apparatus 150 rotates. In addition, although not illustrated, valves may be formed at the channels formed in the disk-type microfluidic apparatus 150 to control the flow of the fluids.

The detection chambers 165 are disposed at equidistant intervals on a circular arc having the same center as the rotation center C of the disk-type microfluidic apparatus 150. The detection chambers 165 are provided with, in advance, various kinds of reagents which cause an optically detectable biochemical reaction with a sample distributed through the distribution channel 162, such as a serum. The optically detectable biochemical reaction can cause a change in absorbance. Although the disk-type microfluidic apparatus 150 illustrated in FIG. 2 is suitable for a biochemical assay, use of the disk-type microfluidic apparatus 150 is not limited thereto. For example, the microfluidic apparatus according to the present invention can also be used for a gene assay or an immunoassay. The blank chambers 166 are not connected to the distribution channel 162, and are filled with distilled water, instead of a sample.

Referring to FIG. 1, the optical detection apparatus 101 includes a rotation operating unit 105 which rotates the disk-type microfluidic apparatus 150. Although the rotation operating unit 105 is not entirely illustrated in FIG. 1, the rotation operating unit 105 can include a motor drive which controls an angular position of the disk-type microfluidic apparatus 150. For example, the motor drive can use a step motor or a direct current motor. Reference numeral 106 denotes a spindle of the rotation operating unit 105 which is to be inserted to the spindle mount groove 152 of the disk-type microfluidic apparatus 150.

The optical detection apparatus 101 further includes: first, second, and third light emission units 107, 109, and 111 which emit light of different wavelength bands from each other; first, second, and third light receiving units 115, 120, and 125; a processor 140; an amplifier 130; an analog to digital (A/D) converter 135; and a memory 145, in which the number of light receiving units is the same as the number of light emission units. Each of the first, second, and third light emission unit 107, 109, and 111 can include a light emitting diode (LED) (not shown) as a light source.

For example, a first LED included in the first light emission unit 107 can be set to emit light of a wavelength band of about 450 nm, a second LED included in the second light emission unit 109 can be set to emit light of a wavelength band of about 500 nm, and a third LED included in the third light emission unit 111 can be set to emit light of a wavelength band of about 600 nm.

The first, second, and third light emission units 107, 109, and 111 are disposed under the disk-type microfluidic apparatus 150 and emit light upward. The first, second, and third light emission units 107, 109, and 111 are disposed equidistant intervals on a circular arc having the same center as the rotation center C of the disk-type microfluidic apparatus 150 such that the first, second, and third light emission units 107, 109, and 111 correspond to the detection chambers 165 of the disk-type microfluidic apparatus 150. Among the detection chambers 165, three adjacent detection chambers 165 can be aligned corresponding one to one to the first, second, and third light emission units 107, 109, and 111. The disk-type microfluidic apparatus 150 is intermittently rotated in a predetermined direction corresponding to an angle between adjacent detection chambers 165 by the rotation operating unit 105. At this time, whenever the disk-type microfluidic apparatus 150 stops, the first, second, and third light emission units 107, 109, and 111 emit light. Thus, when the disk-type microfluidic apparatus 150 makes one complete rotation, each of the detection chambers 165 of the disk-type microfluidic apparatus 150 is sequentially exposed to light emitted from the first, second, and third light emission units 107, 109, and 111.

The first, second, and third light receiving units 115, 120, and 125 are disposed above the disk-type microfluidic apparatus 150 in such a way that the first, second, and third light receiving units 115, 120, and 125 respectively respond to the first, second, and third light emission units 107, 109, and 111, and light emitted from the first, second, and third light emission units 107, 109, and 111 enters the first, second, and third light receiving units 115, 120, and 125 through the detection chambers 165. First, second, and third light pathways L1, L2, and L3, (refer to FIG. 3A) are formed between the first, second, and third light emission units 107, 109, and 111 and the first, second, and third light receiving units 115, 120, and 125. The detection chambers 165 are respectively disposed in the first, second, and third light pathways L1, L2, and L3 to detect properties of a sample.

Figure 3A:
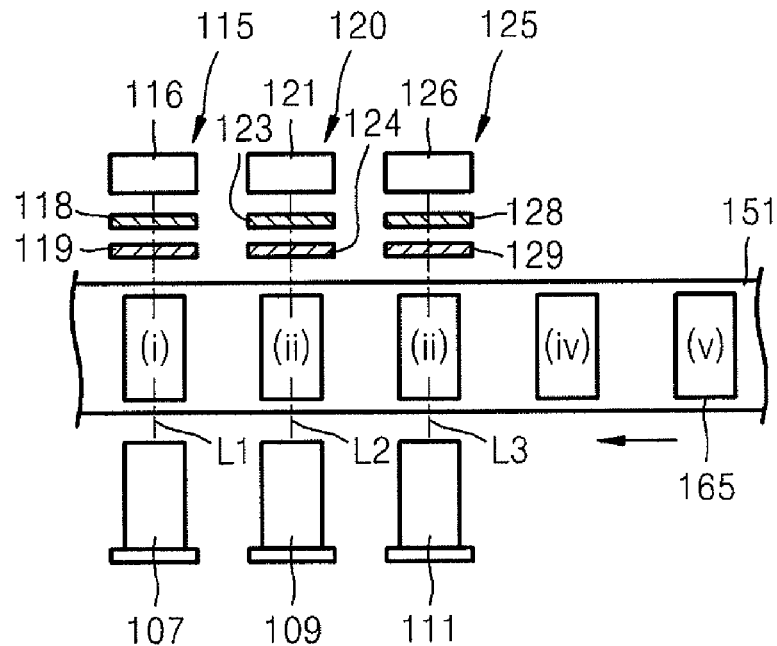
FIGS. 3A through 3C are views illustrating an optical detection method according to an embodiment of the present invention.
Figure 4A:
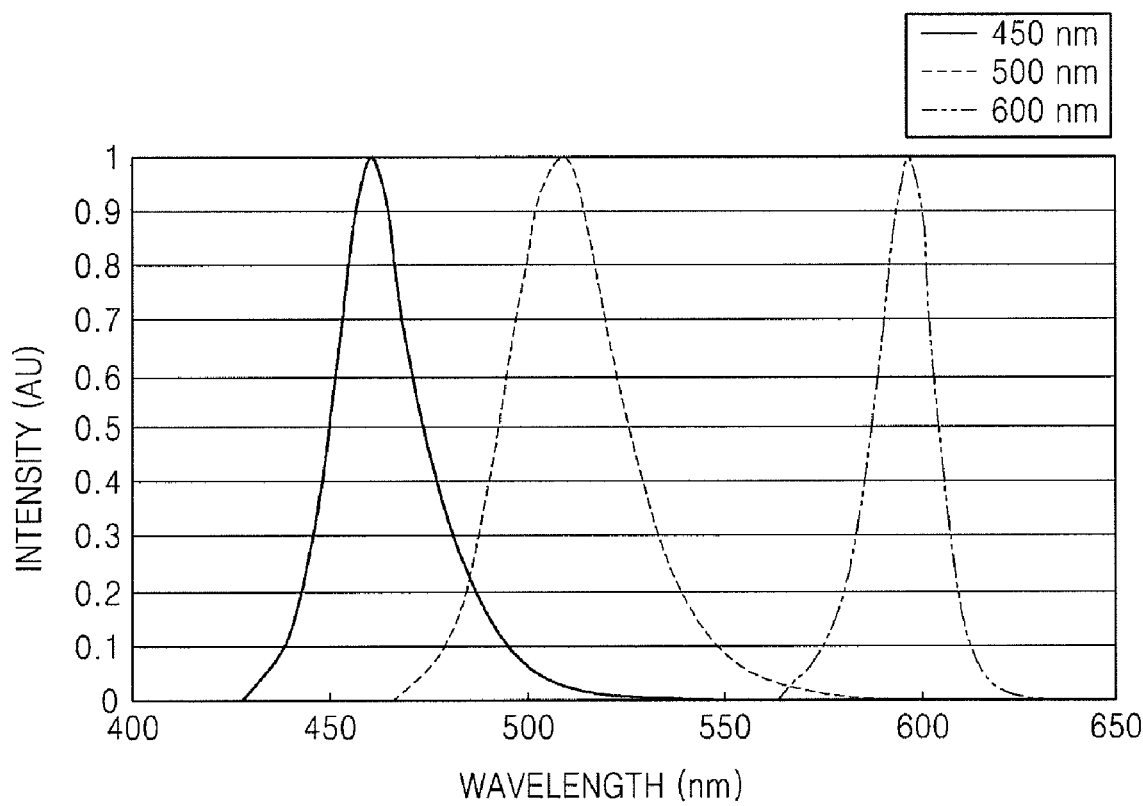
FIGS. 4A and 4B illustrate wavelength bands before and after three kinds of lights emitted from a LED are filtered.
Figure 4B:
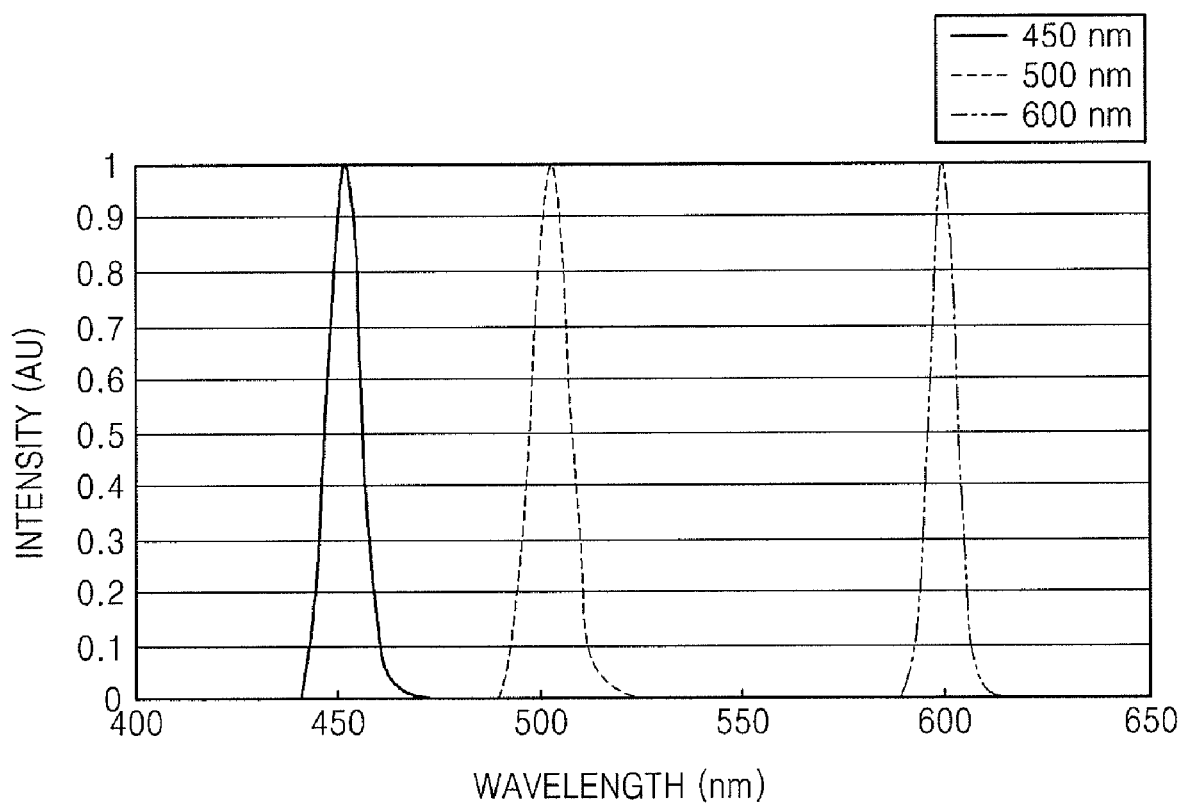

Referring to FIG. 3A, the first, second, and third light receiving units 115, 120, and 125 include photo diodes 116, 121, and 126 which generate electrical signals according to intensity (I) of light, and filtering portions which filter out unwanted wavelength bands of light emitted from the first, second, and third light emission units 107, 109, and 111, respectively. The filtering portions are disposed before the photo diodes 116, 121, and 126 in the light pathways L1, L2, L3. The filtering portions include long wave pass filters 118, 123, and 128 which allow passage of light of a wavelength band which includes a target wavelength and wavelengths relatively longer than the target wavelength, and short wave pass filters 119, 124, and 129 which allow passage of light of a wavelength band which includes a target wavelength and wavelengths relatively shorter than the target wavelength. FIGS. 4A and 4B are graphs illustrating wavelength bands before and after light emitted from three kinds of LED is filtered. Referring to FIGS. 4A and 4B, it can be seen that before the filtering, light emitted from the three kinds of LED have relatively wider wavelength bands, and in contrast, after the filtering, the wavelength bands are narrowed and the wavelengths of the light are highly concentrated at the target wavelengths of 450 nm, 500 nm, and 600 nm. The filtering portion used in embodiments of the present invention is not limited to a filtering portion including a long wave pass filter and a short wave pass filter, and can include other kinds of optical band pass filters.

Referring back to FIG. 1, the optical detection apparatus 101 includes the amplifier 130 which appropriately amplifies an electrical signal generated from the photo diodes 116, 121, 126; the A/D converter 135 which converts an analogue-type electrical signal into a digital-type electrical signal; the processor 140 which measures properties of a sample contained in detection chambers 165 using the digital-type electrical signal; and the memory 145 which stores electrical signal values and software to measure properties of a sample. In embodiments of the present invention, the processor 140 measures absorbance of each of the detection chambers 165, and measures the concentration of a specific component included in the sample based on the absorbance.

Figure 3B:
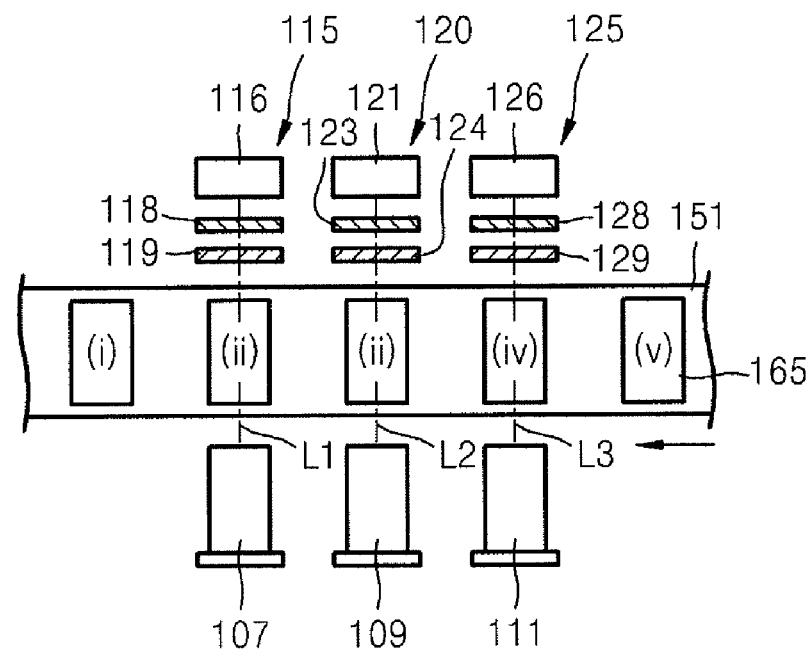
Figure 3C:
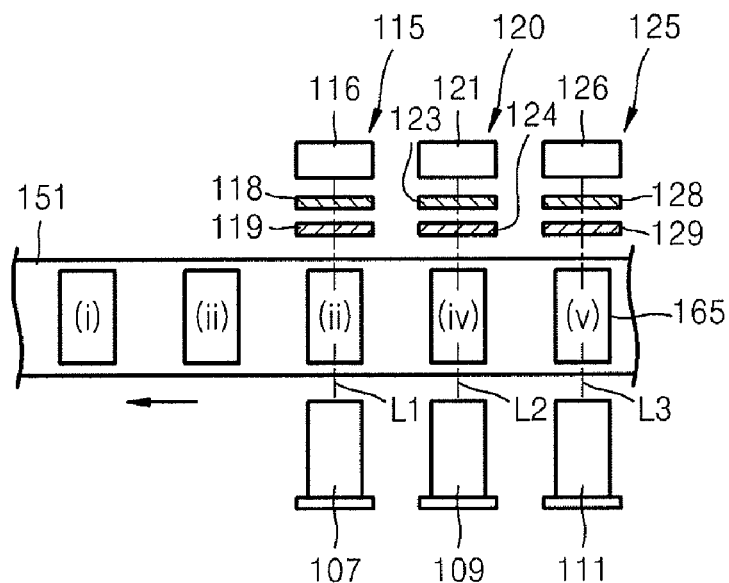

FIGS. 3A through 3C are views illustrating an optical detection method according to an embodiment of the present. The optical detection method according to an embodiment of the present invention will now be described in detail with reference to FIGS. 3A through 3C.

To optically detect properties of a sample, adjacent detection chambers 165 are respectively disposed in first, second, and third light pathways L1, L2, and L3 between first, second, and third light emission units 107, 109, and 111 and first, second, and third light receiving units 115, 120, and 125. Referring to FIG. 3A, a first detection chamber 165(i) is positioned in the first light pathways L1, a second detection chamber 165(ii) is positioned in the second light pathways L2, and the third detection chamber 165(iii) is positioned in the third light pathways L3. The detection chambers 165(i), 165(ii), and 165(iii) can be positioned in such locations by the rotation operating unit 105 (refer to FIG. 1) which controls the rotation angle of the microfluidic apparatus 150.

Meanwhile, before the first, second, and third detection chambers 165(i), 165(ii), and 165(iii) are positioned in the light pathways L1, L2, and L3, a biochemical reaction can occur in each of the detection chambers 165 in advance. Specifically, a sample is distributed to the detection chambers 165 through a distribution channel 162 (refer to FIG. 2) of the disk-type microfluidic apparatus 150, and in each of the detection chambers 165, the distributed sample causes an optically measurable biochemical reaction with various kinds of reagents which have been provided in the detection chamber 165 in advance, which is described above. In general, reaction products may vary according to the kind of a biochemical reaction. Some reaction products show high absorbance with respect to light of a specific wavelength which can be used for detection. Accordingly, a concentration of a specific component, such as cholesterol or alanine aminotransferase (ALT), contained in a sample can be measured by measuring absorbance of light of a specific wavelength band with respect to a specific detection chamber 165.

After the first, second, and third detection chambers 165(i), 165(ii), and 165(iii) are positioned in the first, second, and third light pathways L1, L2, and L3, the first, second, and third light emission units 107, 109, and 111 emit light of different wavelength bands from each other towards the detection chambers 165(i), 165(ii), and 165(iii). Then, the first, second, and third light receiving units 115, 120, and 125 convert light which has passed through the first, second, and third detection chambers 165(i), 165(ii), and 165(iii) into electrical signals. The electrical signals may have different values according to intensity of light entering a photo diode thereof, and are appropriately amplified, converted into a digital type, and then stored in the memory 145. The values of the electrical signals which are stored in the memory 145 corresponds to intensity of light, and may be the values obtained by amplifying and digitalizing by an A/D converter electrical signals to which light received in the first, second, and third light receiving units 115, 120, and 125 is converted. Alternatively, the values of the electrical signals may be average values or total values of the digitalized values obtained for a predetermined period of time.

Then, the disk-type microfluidic apparatus 150 is rotated in a direction illustrated by an arrow of FIG. 1 by an angle corresponding to a distance between adjacent detection chambers 165. As a result, as illustrated in FIG. 3B, the first detection chamber 165(i) is positioned outside the first light pathways L1, the second detection chamber 165(ii) is positioned in the first light pathways L1, the third detection chamber 165(iii) is positioned in the second light pathways L2, and a fourth detection chamber 165 (iv) is positioned in the third light pathways L3. After the second, third, and fourth detection chambers 165(ii), 165(iii), and 165 (iv) are positioned in the light pathways L1, L2, and L3, the first, second, and third light emission units 107, 109, and 111 emit light of different wavelength bands from each other towards the second, third, and fourth detection chambers 165(ii), 165(iii), and 165 (iv). Then, the first, second, and third light receiving units 115, 120, and 125 convert the light which has passed through the second, third, and fourth detection chambers 165(ii), 165(iii), and 165 (iv) into electrical signal. The electrical signals obtained are stored in the memory 145.

Then, the disk-type microfluidic apparatus 150 is rotated in the direction illustrated by an arrow of FIG. 1 by an angle corresponding to a distance between adjacent detection chambers 165. As a result, as illustrated in FIG. 3C, the second detection chamber 165(ii) is positioned outside the first light pathways L1, the third detection chamber 165(iii) is positioned in the first light pathway L1, the fourth detection chamber 165 (iv) is positioned in the second light pathway L2, and a fifth detection chamber 165 (v) is positioned in the third light pathway L3. After the third, fourth, and fifth detection chambers 165(iii), 165 (iv), and 165(v) are positioned in the light pathways L1, L2, and L3, the first, second, and third light emission units 107, 109, and 111 emit light of different wavelength bands from each other towards the third, fourth, and fifth detection chambers 165(iii), 165 (iv), and 165(v). Then, the first, second, and third light receiving units 115, 120, and 125 convert the light which has passed through the third, fourth, and fifth detection chambers 165(iii), 165 (iv), and 165(v) into electrical signals. The electrical signals obtained are stored in the memory 145.

When the disk-type microfluidic apparatus 150 has made one complete rotation with intermittences, light emitted from the first, second, and third light emission units 107, 109, and 111 can sequentially be incident on the detection chambers 165 and a blank chamber 166 (refer to FIG. 2) which is included in the disk-type microfluidic apparatus 150, so that light intensity data with respect to the detection chambers 165 and the blank chamber 166 can be measured.

The processor 140 (refer to FIG. 1) measures the concentration of a material contained in the sample using the light intensity data obtained. The absorbance can be defined using Equation 1:

$$A = -\log I/I_0 \quad \text{[Equation 1]}$$

where A denotes absorbance, $I_0$ denotes intensity of light after the light passes through the blank chamber, and I denotes intensity of light after the light passes through the sample chamber. If Equation 1 complies with Iambert-Beer's law, absorbance can also be defined by Equation 2.

$$A = -\log I/I_0 = \epsilon C d \quad \text{[Equation 2]}$$

where $\epsilon$ denotes adsorption coefficient, C denotes a concentration of a specific component contained in a fluid, and d denotes a thickness of a fluid layer. Through Equation 2, the concentration of a specific component can be measured using the light intensity data corresponding to the detection chamber 165 and the blank chamber 166 when values of the absorbance coefficient $\epsilon$ and the thickness of the fluid layer d are obtained. For example, in the case that a biochemical reaction which leads to an optical detection of cholesterol occurs in the first detection chamber 165(i), the absorbance A can be obtained using intensity of light (denoted by I in Equation 1) obtained when the detection chamber 165(i) is positioned in the second light pathway L2 and the intensity of light (denoted by $I_0$ in Equation 1) obtained when the blank chamber 166 is positioned in the second light pathway L2, since the reaction product of the biochemical reaction strongly absorbs light of a wavelength of 500 nm. Then, the concentration of cholesterol can be obtained through Equation 2. Meanwhile, if there is a reference sample of which absorbance and the concentration of cholesterol of the reference sample corresponding to the absorbance are known through an identical biochemical reaction, the concentration C of cholesterol of a sample to be assayed can be measured using a proportion between the concentration of cholesterol of the reference sample Cs and absorbance. That is, through an equation given by C=A×Cs/As, the concentration C of cholesterol of a sample can be measured.

Such detection of cholesterol can be performed using light intensity data obtained after enough time for a chemical reaction to occur, which can be referred to as 'one point assay.' The one point assay can be also performed after a reaction is stopped by adding an acid or alkali thereto, or during the reaction.

Meanwhile, an alanine aminotransferase (ALT) that belongs to a liver panel can be detected using a reaction rate of an enzyme. That is, a change in the amount of a substrate per minute can be measured using absorbance $A_1$ which is measured at time $t_1$ and absorbance $A_2$ which is measured at $t_2$: $(A_2-A_1)/(t_2-t_1)$. Then, the change can be multiplied by a constant. As a result, ALT that is an enzyme can be quantified.

For example, in the case of detection of ALT, a sample is distributed to detection channels 165 and a biochemical reaction is performed for one minute. Then, one complete rotation of a disk-type microfluidic apparatus 150 is made, and light intensity data is obtained and absorbance is measured. Three minutes after the biochemical reaction begins, one more complete rotation of the disk-type microfluidic apparatus 150 is made, and light intensity data is obtained and absorbance is measured. ALT can be measured using Equation 3:

ALT($IU$/mL)=[$A$(3 minutes)−$A$(1 minute)/(2 minute)]/ [6.22$d$×dilution rate] [Equation 3]

In Equation 3, 6.22 is a millimolar absorptivity of NADH that is a substrate, and d is a thickness of a fluid layer as in Equation 2. Through Equation 3, the concentration of NADH which reacts for two minutes can be obtained by dividing the difference in absorbance between when the reaction occurs for 3 minutes and when the reaction occurs for 1 minute, that is, the value of A (3 minutes)−A (1 minute) by millimolar absorptivity, that is, 6.22 and a thickness of a fluid layer, that is, d. As a result, the amount of ALT in a reaction solution can be measured. Since the sample is mixed with the reaction solution and the sample is thus diluted, the diluted value can be compensated by dividing the amount of ALT in the reaction solution with a dilution rate, that is, 'sample volume/ entire volume.' In such a way described above, the amount of ALT in the sample can be measured.

Meanwhile, the speed of an enzyme reaction can be measured through regression analysis using data measured at three or more points during the reaction.

Although the optical detection apparatus illustrated in the drawings includes three light emission unit-light receiving unit pairs, the present invention is not limited thereto. For example, an optical detection apparatus according to the present invention can further include other light emission units which emit light of various wavelength bands different from each other.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An optical detection apparatus comprising:
at least one light emission unit which emits light of a predetermined wavelength band;
at least one light receiving unit which is disposed such that the light receiving unit receives the light emitted from the light emission unit and generates an electrical signal according to the intensity of the light received, wherein the number of light receiving units is the same as the number of light emission units;
a rotation operating unit which rotates a disk-type microfluidic apparatus comprising at least one detection chamber in which a sample is to be loaded and at least one blank chamber in which a reference sample is to be loaded, the rotation being performed such that the detection chamber and the blank chamber are disposed in a light pathway between a light emission unit-light receiving unit pair; and
a processor which measures a property of the sample contained in the detection chamber using the electrical signals generated by the light receiving unit.

2. The optical detection apparatus of claim 1, wherein the optical detection apparatus comprises a plurality of light emission unit-light receiving unit pairs, the light emission unit and the light receiving unit of each pair corresponding to each other, so that light is simultaneously emitted towards at least some of the detection chambers of the disk-type microfluidic apparatus and the electrical signal corresponding to the emitted light is obtained, wherein the light emission units emit light of different wavelength bands from each other.

3. The optical detection apparatus of claim 2, wherein the plurality of light emission unit—light receiving unit pairs are disposed at equidistant intervals on a circular arc having the same center as a rotation center of the disk-type microfluidic apparatus.

4. The optical detection apparatus of claim 3, wherein when the disk-type microfluidic apparatus makes one complete rotation, each of the detection chambers of the disk-type microfluidic apparatus is sequentially exposed to light emitted from each of the light emission units.

5. The optical detection apparatus of claim 1, wherein the light emission unit comprises a light emitting diode (LED).

6. The optical detection apparatus of claim 1, wherein the light receiving unit comprises a photo diode.

7. The optical detection apparatus of claim 1, wherein the light receiving unit further comprises a filtering portion which reduces a width of a wavelength band of light emitted from the light emission unit.

8. The optical detection apparatus of claim 7, wherein the filtering portion comprises a long wave pass filter which allows passage of light of a wavelength band which includes a target wavelength and wavelengths longer than the target wavelength, and a short wave pass filter which allows passage of light of a wavelength band which includes a target wavelength and wavelengths shorter than the target wavelength.

9. The optical detection apparatus of claim 1, wherein the processor measures intensity of the light passed through the detection chamber.

10. The optical detection apparatus of claim 9, wherein the property of the sample determined by the apparatus is the concentration of a specific material measured on the basis of absorbance of the sample proportional to the concentration of the specific component.

11. A microfluidic system comprising a disk-type microfluidic apparatus comprising at least one detection chamber in which a sample is to be loaded and at least one blank chamber in which a reference sample is to be loaded, and an optical detection apparatus which optically measures a property of the sample contained in the detection chamber, the optical detection apparatus comprising:
at least one light emission unit which emits light of a predetermined wavelength band;
at least one light receiving unit which is disposed such that the light receiving unit receives the light emitted from the light emission unit and generates an electrical signal according to the intensity of the light received, wherein the number of light receiving units is the same as the number of light emission units;
a rotation operating unit which rotates the disk-type microfluidic apparatus such that the detection chamber and the blank chamber are disposed in a light pathway between the light emission unit and the light receiving unit; and
a processor which measures the property of the sample contained in the detection chamber using the electrical signal generated by the light receiving unit.

12. The microfluidic system of claim 11, wherein the disk-type microfluidic apparatus comprises a plurality of the detection chambers,
the optical detection apparatus comprises a plurality of light emission unit—light receiving unit pairs, the light emission unit and the light receiving unit of each pair corresponding each another, so that light is simultaneously emitted to at least some of the detection chambers of the disk-type microfluidic apparatus and the electrical signal corresponding to the light emitted is obtained, and the light emission units emit light of different wavelength bands from each other.

13. The microfluidic system of claim 12, wherein the detection chambers are disposed at equidistant intervals on a circular arc having the same center as a rotation center of the disk-type microfluidic apparatus, and a plurality of light emission unit—light receiving unit pairs are disposed at equidistant intervals on the circular arc having the same center as a rotation center of the disk-type microfluidic apparatus such that the plurality of the light emission unit—light light receiving unit pairs correspond to the detection chambers.

14. The microfluidic system of claim 13, wherein the rotation operating unit rotates the disk-type microfluidic apparatus with intermittences corresponding to a distance between adjacent detection chambers in one direction, and each of the detection chambers of the disk-type microfluidic apparatus is sequentially exposed to light emitted from each of the light emission units when the disk-type microfluidic apparatus makes one complete rotation.

15. The microfluidic system of claim 11, wherein the light emission unit comprises a light emitting diode (LED).

16. The microfluidic system of claim 11, wherein the light receiving unit comprises a photo diode.

17. The microfluidic system of claim 11, wherein the light receiving unit further comprises a filtering portion which reduces a width of a wavelength band of light emitted from the light emission unit.

18. The microfluidic system of claim 17, wherein the filtering portion comprises a long wave pass filter which allows passage of light of a wavelength band which includes a target wavelength and wavelengths longer than the target wavelength, and a short wave pass filter which allows passage of light of a wavelength band which includes a target wavelength and wavelengths shorter than the target wavelength.

19. The microfluidic system of claim 11, wherein the processor measures intensity of the light passed through the detection chamber.

20. The microfluidic system of claim 19, wherein the property of the sample determined by the apparatus is the concentration of a specific material measured on the basis of absorbance of the sample proportional to the concentration of the specific component.

21. The microfluidic system of claim 11, wherein the reference sample is a reference fluid.

22. An optical detection method for a disk-type microfluidic apparatus comprising at least one detection chamber containing a sample and at least one blank chamber containing a reference sample, the method comprising:

positioning the detection chamber and the blank chamber of the disk-type microfluidic apparatus in a light pathway between a light emission unit and a light receiving unit;

emitting light of a predetermined wavelength band towards the detection chamber, using the light emission unit;

receiving the light which has passed through the detection chamber and converting the light into an electrical signal, using the light receiving unit; and measuring a property of the sample contained in the detection chamber using the electrical signal.

23. The optical detection method of claim 22, wherein the disk-type microfluidic apparatus comprises a plurality of detection chambers, and a plurality of light emission unit—light receiving unit pairs, wherein the light emission units emit light of different wavelength bands from each other and the light receiving units receive the light emitted, the positioning is performed such that at least some of the detection chambers of the disk-type microfluidic apparatus are positioned in light pathways between the plurality of light emission unit—light receiving unit pairs, the emitting is performed such that the light emission units simultaneously emit light of different wavelength bands from each other to at least some of the detection chambers, the receiving of light is performed such that the light receiving units convert the light which has passed through at least some of the detection chambers into an electrical signal, and the measuring is performed such that a property of a sample contained in the at least some of the detection chambers is measured using the electrical signal.

24. The method of claim 23, wherein the detection chambers are disposed at equidistant intervals on a circular arc having the same center as a rotation center of the disk-type microfluidic apparatus, and when the disk-type microfluidic apparatus makes one complete rotation, each of the detection chambers of the disk-type microfluidic apparatus are sequentially exposed to light of each of the light emission units.

25. The method of claim 22, wherein in the measuring, intensity of the light passed through the detection chamber is measured.

26. The method of claim 25, wherein after the measuring, absorbance of the detection chamber is calculated and a concentration of a specific components contained in the sample is determined on the basis of the absorbance.

* * * * *